United States Patent
Mansi

(10) Patent No.: US 11,420,051 B2
(45) Date of Patent: Aug. 23, 2022

(54) MEDICAL DEVICE FOR TREATING DIABETES

(71) Applicant: Imam Abdulrahman Bin Faisal University, Dammam (SA)

(72) Inventor: Ahmed Abdelkarim Mansi, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 359 days.

(21) Appl. No.: 15/982,486

(22) Filed: May 17, 2018

(65) Prior Publication Data

US 2019/0351228 A1 Nov. 21, 2019

(51) Int. Cl.
*A61B 5/00* (2006.01)
*A61N 1/36* (2006.01)
*A61B 5/145* (2006.01)

(52) U.S. Cl.
CPC ...... *A61N 1/36007* (2013.01); *A61B 5/14532* (2013.01); *A61B 5/425* (2013.01)

(58) Field of Classification Search
CPC ............ A61N 1/36007; A61B 5/14532; A61B 5/425; A61B 7/00; A61H 23/0245
See application file for complete search history.

(56) References Cited

U.S. PATENT DOCUMENTS

| | | | |
|---|---|---|---|
| 5,919,216 A | 7/1999 | Houben et al. | |
| 7,856,260 B1* | 12/2010 | Ryu | A61B 5/283 600/375 |
| 2004/0249421 A1 | 12/2004 | Harel et al. | |
| 2006/0184207 A1* | 8/2006 | Darvish | A61N 1/36007 607/40 |
| 2007/0060812 A1* | 3/2007 | Harel | A61B 5/425 600/347 |
| 2008/0045882 A1* | 2/2008 | Finsterwald | A61N 7/00 604/22 |
| 2009/0292204 A1* | 11/2009 | Pansky | A61B 8/488 600/439 |
| 2011/0021965 A1* | 1/2011 | Karp | A61L 15/64 602/54 |
| 2011/0178441 A1* | 7/2011 | Tyler | A61B 5/0476 601/2 |
| 2012/0267986 A1* | 10/2012 | Galluzzo | B06B 1/0603 310/348 |
| 2013/0102867 A1* | 4/2013 | Desborough | A61B 5/7275 600/365 |

(Continued)

FOREIGN PATENT DOCUMENTS

| | | |
|---|---|---|
| CN | 201542925 U | 8/2010 |
| WO | 2004/052208 A1 | 6/2004 |
| WO | 2007/007339 A2 | 1/2007 |

OTHER PUBLICATIONS

Resorba, "Suture Manual", 2011 (Year: 2011).*
Rengarajan, "Pancreatic duct diameter" (Year: 2021).*

*Primary Examiner* — Amanda Lauritzen Moher
*Assistant Examiner* — Brooke Lyn Klein
(74) *Attorney, Agent, or Firm* — Oblon, McClelland, Maier & Neustadt, L.L.P.

(57) ABSTRACT

A medical device containing a sensor, a motor, one or more plates, and a control unit, for treating diabetes. The medical device vibrates the pancreas thereby improving blood and secretory hormone circulation and enhancing the production of insulin.

7 Claims, 6 Drawing Sheets

(56) References Cited

U.S. PATENT DOCUMENTS

| | | | | |
|---|---|---|---|---|
| 2014/0336743 A1* | 11/2014 | Zotz | ............................ | A61F 2/82 |
| | | | | 600/509 |
| 2015/0073445 A1* | 3/2015 | Griffin | ..................... | A61L 27/56 |
| | | | | 606/151 |
| 2016/0236012 A1* | 8/2016 | Zderic | ....................... | A61N 7/00 |
| 2017/0209717 A1* | 7/2017 | Bonutti | ................... | A61B 34/76 |
| 2019/0216438 A1* | 7/2019 | Song | ....................... | A61B 8/461 |

\* cited by examiner

MEDICAL DEVICE FOR TREATING DIABETES

FIELD OF THE INVENTION

This disclosure relates to medical implants, and particularly to a medical device which vibrates a pancreas for treating diabetes.

DESCRIPTION OF THE RELATED ART

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Diabetes has been known to be an irreversible disorder leading to increased blood glucose levels. Current type 1 diabetes treatment includes administering insulin, exercising, and making dietary changes. Current type 2 diabetes treatment includes administering insulin and/or non-insulin medications, exercising to reduce weight, or making dietary changes. Globally, the cost of treating diabetes is high. The average of lifetime cost of treating diabetes in the U.S.A. is $85,000.

In view of the foregoing, one objective of the present disclosure is to provide a medical device for treating diabetes while lowering the treatment cost by reducing the use of anti-diabetes drugs and/or home blood glucose tests, and reducing hospitalization and complications related to diabetes.

SUMMARY OF THE DISCLOSURE

A first aspect of the disclosure relates to a medical device, comprising: (i) a glucose sensor; (ii) a motor; (iii) at least one plate, where the at least one plate is connected to the motor, and the plate and motor are implantable; and (iv) a control unit which is in communication with the motor and the glucose sensor.

In one embodiment, the medical device further comprises an internal unit.

In one embodiment, the motor is a vibration motor.

In one embodiment, the plate is in direct contact with the motor.

In one embodiment, the motor is an ultrasonic transducer.

In one embodiment, the at least one plate is flexible and configured to conform to a surface of the pancreas.

In one embodiment, the at least one plate has a curve shape configured to contact a surface of a pancreas.

In one embodiment, the at least one plate has a length in a range of 10-200 mm.

In one embodiment, the length is in a range of 15-50 mm.

In one embodiment, the at least one plate has a breadth in a range of 1-25 mm.

In one embodiment, the at least one plate has a thickness in a range of 0.1-2 mm.

In one embodiment, the at least one plate comprises a surface comprising a plurality of protrusions.

In one embodiment, an average height of the plurality of protrusions is 0.02-2 mm.

In one embodiment, the at least one plate comprises silicone.

In one embodiment, the control unit is configured to actuate the motor to vibrate the pancreas via the at least one plate.

In one embodiment, the control unit is configured to actuate and deactuate the motor based on a blood glucose level feedback from the glucose sensor, thereby keeping a blood glucose level within a range of 70-140 mg/dl.

In one embodiment, the control unit comprises: (i) a display; (ii) at least one battery; and (iii) a central processing unit electrically connected to the motor and the glucose sensor.

A second aspect of the disclosure relates to a method for treating diabetes, comprising:
implanting the medical device of the first aspect in a subject in need thereof whereby the at least one plate is in direct contact with a pancreas;
detecting a blood glucose level in the subject with the glucose sensor; and
vibrating the pancreas when the blood glucose level is higher than 140 mg/dl for an effective duration until the blood glucose level measures within the range of 70-140 mg/dl.

In one embodiment, the effective duration is in a range of 1 second to 30 minutes.

In one embodiment, the pancreas is vibrated at a frequency in a range of 50-100 Hz.

The foregoing description is intended to provide a general introduction and summary of the present disclosure and is not intended to be limiting in its disclosure unless otherwise explicitly stated. The presently preferred embodiments, together with further advantages, will be best understood by reference to the following detailed description taken in conjunction with the accompanying drawings.

DETAILED DESCRIPTION OF THE DISCLOSURE

Figure 1:
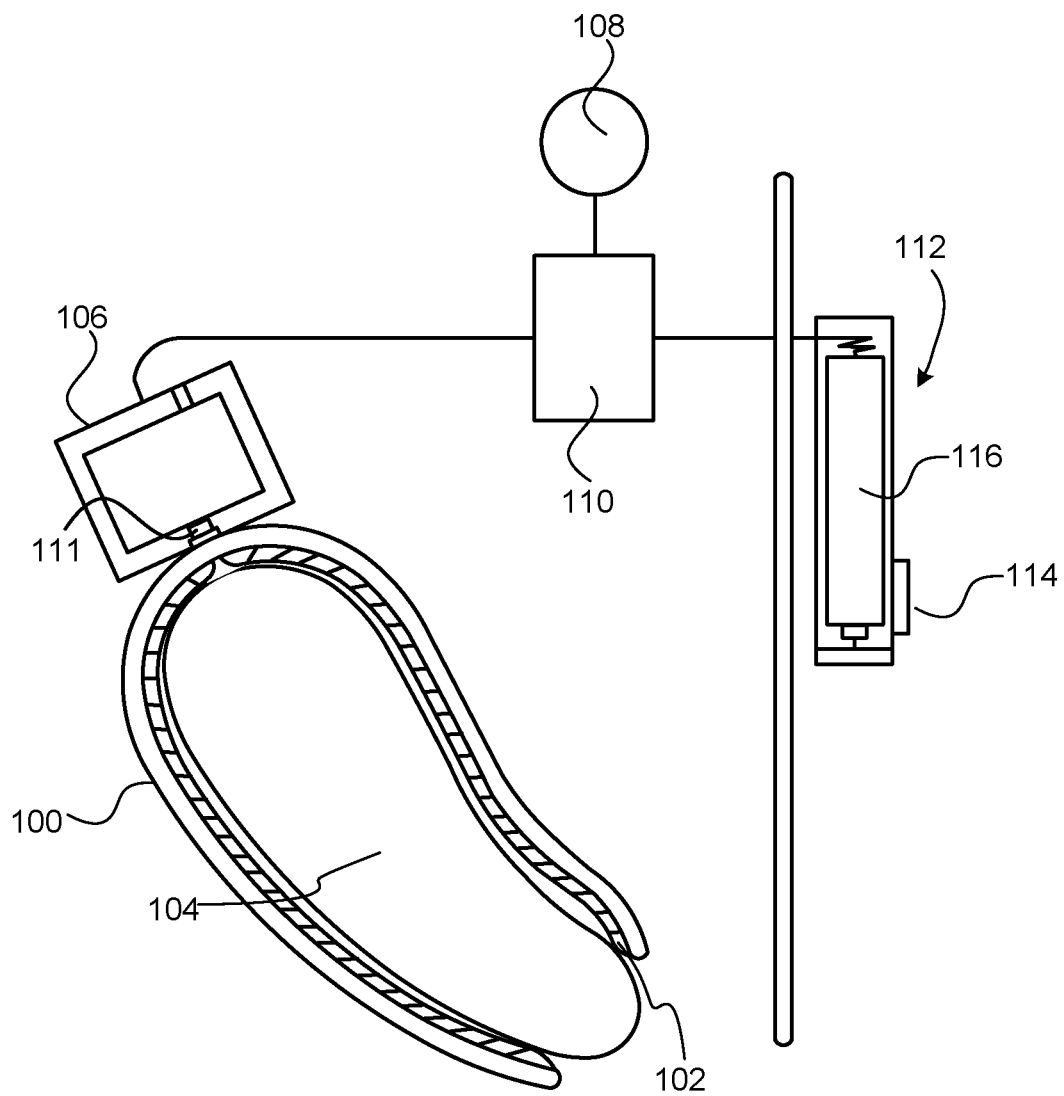
FIG. 1 shows an embodiment of the medical device with implanted and external components.

Embodiments of the present disclosure will now be described more fully hereinafter with reference to the accompanying drawings, in which some, but not all embodiments of the disclosure are shown.

Within the description of this disclosure, where a numerical limit or range is stated, the endpoints are included unless stated otherwise. Also, all values and subranges within a numerical limit or range are specifically included as if explicitly written out. As used herein, the words "a" and "an" and the like carry the meaning of "one or more".

As used herein, "an implantable element" or "an implanted element" refers to any component of the medical device that is totally or partly introduced, surgically or medically, into the body of a subject (a human or an animal) or by medical intervention into a natural orifice, and which is intended to remain there after the procedure.

As used herein, the terms "treat", "treatment", and "treating" refer to the reduction or inhibition of the progression and/or duration of a disease (e.g., diabetes), and/or the reduction or amelioration of the severity of the disease. With regard to the disease, these terms may mean that one or more of the symptoms of the disease will be reduced. Such terms may refer to at least one result: (1) a level of hemoglobin A1c, HbA1c, or glycohemoglobin is not higher than 7%, 6.5%, 6%, or preferably below 5.7%; (2) relieving to some extent (or, preferably, eliminating) one or more side effects (e.g., low blood glucose, stomach gas, bloating, skin rash or itching, weight gain, kidney complications, tiredness or dizziness, diarrhea, risk of liver disease, anemia risk, swelling of legs or ankles) associated with taking diabetes medication; (3) relieving to some extent (or, preferably, eliminating) one or more side effects (e.g., fatigue, increased thirst, blurry vision, dizziness, irritability, sweating, weakness, lack of coordination, and frequent urination) associated with the diabetes; and (4) a reduction in occurrences of blood glucose spikes beyond 140 mg/dl or blood glucose swings (from less than 70 mg/dl to more than 140 mg/dl).

In some embodiments, "treating" or "treatment" of the disease includes preventing the disease from occurring in a subject that may be predisposed to the disease but does not yet experience or exhibit symptoms of the disease (prophylactic treatment), and inhibiting the disease (slowing or arresting its development). Prediabetes subjects have a blood glucose level higher than normal but not high enough to be diabetic. For example, prediabetes subjects may have an level of hemoglobin A1c between 5.7-6.4% and/or a fasting blood glucose level of 100-125 mg/dl.

The terms "patient", "subject", and "individual" are used interchangeably. As used herein, they refer to individuals suffering from a disease and encompass mammals. None of the terms require that the individual be under the care and/or supervision of a medical professional. Mammals are any member of the mammalian class, including but are not limited to humans, non-human primates, such as chimpanzees, and other apes and monkey species, farm animals, such as cattle, horses, sheep, goats, swine, domestic animals, such as rabbits, dogs, and cats, laboratory animals including rodents, such as rats, mice and guinea pigs, and the like. In some embodiments, the subjects are mice and/or rhesus monkeys as these two species have well-established diabetes models. In preferred embodiments, the subject is a diabetic person or a prediabetic person.

Current diabetic treatment includes: (i) administering insulin with syringes, pre-filled pens, and/or insulin pump, (ii) increasing insulin sensitivity, (iii) increasing glucose excretion, and/or (iv) decreasing absorption of carbohydrates from the digestive tract.

The presently disclosed medical device increases pancreatic insulin production by vibrating the pancreas thereby improving the blood circulation in the pancreas and the function of the pancreas. Consequently, enhancement in the production of the necessary hormones (e.g., insulin, glucagon, and somatostatin) for keeping the blood glucose level in the acceptable range for diabetic subjects occurs. The acceptable range of blood glucose level (without fasting) may be at least 70 mg/dl, 80 mg/dl, 90 mg/dl, and up to 120 mg/dl, 130 mg/dl, or 140 mg/dl. An advantage of this device is that the subject may avoid diabetes medication that may have serious side effects (e.g., hypoglycemia) when administered for an extended period of time.

The diabetes may be a polygenic form of diabetes (e.g., type 1 diabetes, type 2 diabetes), a monogenic form of diabetes (e.g., neonatal diabetes mellitus, maturity-onset diabetes of the young), or cystic fibrosis-related diabetes. The term "polygenic" refers to the risk of developing these forms of diabetes is related to multiple genes. The term "monogenic" refers to rare forms of diabetes result from mutations in a single gene. In subjects diagnosed with cystic fibrosis-related diabetes, a thick, sticky mucus that is characteristic of the disease causes scarring of the pancreas. This scarring may prevent the pancreas from producing enough insulin so the subjects become insulin deficient.

An aspect of the invention relates to a medical device, comprising: (1) a glucose sensor; (2) a motor; (3) at least one plate; and (4) a control unit. In some embodiments, the medical device further comprises an internal unit. These elements may be implanted in or located external to a subject. The implanted element(s) may be located inside the subject's abdomen and around the pancreas. The implanted elements may be made of high quality medical grade materials described hereinafter to minimize or eliminate any undesirable tissue reaction which may lead to rejection of the implanted part. The implanted element(s) may be lightweight (e.g., each implanted element may weigh 0.1-5 g, 0.5-3 g, or 1-2 g). The implanted element(s) may be attached to the subject's tissues by, for example, sutures, staples, tacks, tissue glues, sealants, and hooks. The hooks, sutures, staples, and/or tacks may be made of the materials described herein or materials known to those of skill in the art.

In some embodiments, nanoparticles may be incorporated into or coated onto a surface of the implanted element(s) to confer advantageous therapeutic, diagnostic, and biocompatibility properties. A coating thickness of the nanoparticles may be 10-100 μm, 20-70 μm, or 30-50 μm. The implanted element(s) may contain 0.01-10 wt %, 0.1-5 wt %, or 1-3 wt % of the nanoparticles, based on a total weight of the implanted element(s). Superparamagnetic iron oxide nanoparticles may be integrated into or coated onto a surface of the implanted element(s) such that the implanted element(s) becomes visible in magnetic resonance imaging (MRI) (Investigation of superparamagnetic iron oxide nanoparticles for MR-visualization of surgical implants, Slabu I, Guntherodt G, Schmitz-Rode T, Hodenius M, Kramer N, Donker H, Krombach G A, Otto J, Klinge U, Baumann M, Curr Pharm Biotechnol. 2012 March; 13(4):545-51, incorporated herein by reference in its entirety). In another embodiment, graphene oxide and silver nanoparticles may be incorporated into or coated onto a surface of the implanted element(s) to stop bleeding and disinfect the surgery wound. In some embodiments, the implanted element(s) may be coated with high-purity and adherent titanium dioxide nanoparticles for improved biocompatibility.

The implanted element(s) may comprise a medication to promote tissue healing. The medication may be stored in a microchip, which is attached to the implanted elements. The medication may also be in a form of a paste, which is applied onto the elements. Preferably, the medication is applied onto a patch, which can stick on the elements. The patch may be made of a resorbable material, such as alpha-polyesters or poly-(alpha-hydroxy) acids, which degrade with the healing process so that the medication is transferred to the healing tissue. The medication may include an antibiotic (e.g., ampicillin, amoxicillin, and benzylpenicillin) to combat infection.

The at least one plate 100 may be implanted on the peritoneum lining of the pancreas 104 or between the peritoneum lining and the pancreas 104. The at least one plate 100 may be in direct contact with at least a part of the subject's pancreas 104. Preferably, the at least one plate 100 covers at least 50%, 60%, 70%, 80%, 90%, 95%, or 99% of a surface area of the pancreas 104 because the islets of Langerhans responsible for insulin production are distributed all over the pancreas 104. The at least one plate 100 may be in direct contact with the motor 106, for example, as shown in FIG. 1.

The at least one plate 100 may have a length in a range of 10-200 mm, 50-170 mm, or 100-150 mm. In some embodiments, the length, l, of the at least one plate 100 is in a range of 15-50 mm or 20-30 mm. The length of the at least one plate 100 is the distance measured from a first edge to a second edge located furthest from the first edge (see FIG. 2A). A breadth, b, of the at least one plate 100 is in a range of 1-25 mm, 5-20 mm, or 8-15 mm. A thickness, t, of the at least one plate 100 may be in a range of 0.1-2 mm, 0.5-1.5 mm, 1-1.1 mm. The at least one plate 100 may have a uniform thickness throughout the plate or a tapered thickness. For example, the at least one plate may be thicker in the middle portion and thinner at the edges. The middle portion may be 0.2-1 mm thicker, 0.5-0.8 mm, or 0.6-0.7 mm thicker than the edges. When the plate 100 has a tapered thickness, the cross-section of the plate may be one of the shapes shown in FIGS. 2B, 2C, and 2D, and surface 124 may be in direct contact with the pancreas.

The pancreas is shaped like a flat pear. The at least one plate 100 may be molded so to have the same shape of the pancreas 104. It may be desirable to first measure or "size" the curvature of the pancreas 104 where the plate 100 is to be implanted. The measurement may be performed using one or more methods that are known to those skilled in the art. Such methods include, without limitation, ultrasound and computer axial tomography. In some embodiments, the at least one plate 100 has a curve shape configured to contact a surface of a pancreas 104. A girth of the plate 100 ranges from more than 0.2 cm to 3.5 mm, preferably more than 0.2 mm to 1.7 mm, more preferably more than 0.2 to 1.2 mm. The term "girth", as used herein, refers to a length around a curve. A chord of the plate 100 ranges from 0.2-3 mm, preferably 0.2-1.5 mm, more preferably 0.2-1 mm. The term "chord", as used herein, refers to a straight line segment between two opposing ends of the curve. A depth of a curve of the plate 100 may range from 0.05-0.5 mm, preferably 0.1-0.3 mm, more preferably 0.1-0.2 mm. The term "depth of a curve", as used herein, refers to a shortest distance between the chord and a highest point of the curve. In some embodiments, the at least one plate 100 is flexible and configured to conform to a surface of the pancreas 104.

The pancreas has a head (a wide end of the pancreas), neck, body, and tail (a narrow end of the pancreas). The head is nestled in the curve of the duodenum and may be difficult to access. Therefore, the implanted elements may be located on or near the neck, body, and/or tail of the pancreas. In some embodiments, the at least one plate 100 conforms to and aligns with the curved head of the pancreas and the motor is attached to the at least one plate 100 by stitching, staples, tacks, and/or hooks. The at least one plate 100 may be oriented such that its longitudinal axis is parallel or substantially parallel (e.g., no more than 7°, no more than 5°, or no more than 3°) to the longitudinal axis of the pancreas.

In some embodiments, the at least one plate 100 may be oriented such that its longitudinal axis is transverse to the longitudinal axis of the pancreas and the medical device may still function as intended.

The at least one plate 100 may contain silicone (e.g., dimethicone, methicone, phenyl trimethicone, and cyclomethicone) and/or a carbon-based polymer. The silicone may be a medical grade silicone (e.g., at least Class VI certified). Exemplary carbon-based polymers include, without limitation, a polyester, a nylon, an acacia gum, a collagen (e.g., a types 1-13), a chitosan, a polyether sulfone, a fluoroelastomer (e.g., polytetrafluoroethylene (PTFE), expanded polytetrafluoroethylene (e-PTFE)), a polyimide, a polycarbonate, a polyethylene, a polyacrylate, a polyethylene glycol, a polyurethane, a polyglycolic acid (PGA), a polyglactin (PGA-PLA), a polycaprolactone, a polydioxanone, a polyglyconate (a copolymer of trimethilene carbonate and glycolide), a polyorthoester, a polyanhydride, a polyhydroxybutyrate, a poly-DL-lactic acid (DL-PLA), a poly-L-lactic acid (L-PLA), a poly-D-lactic acid (D-PLA), and combinations and/or copolymers thereof.

The at least one plate 100 may or may not contain a mesh on at least a part of the surface of the plate 100. For example, the mesh may cover up to 50%, 60%, 70%, 80%, 90%, or 100% of the surface area of the plate 100. The mesh may be in direct contact with the peritoneal lining and/or tissue near the pancreas 104. In some embodiments, there is an overlap of the mesh which can be sutured to the subject's tissue/pancreas 104. The mesh may be made of or may be coated with materials that provide a slick or lubricating function, such as synthetic polymers and/or biopolymers, to help neutralize vibration and friction side effects of the disclosed medical device. The mesh may or may not contain resorbable materials. For example, the mesh may contain up to 5 wt %, 4 wt %, 3 wt %, 2 wt %, or 1 wt % of the resorbable material, based on a total weight of the mesh. Resorbable materials can be broken down by hydrolysis or proteolytic enzymatic degradation taking place after implanting the at least one plate 100. These chemical processes dissolve, degrade, or disintegrate a part of the mesh in the body of the subject.

Examples of synthetic polymers include, without limitation, polyethylene, polypropylene, polyester, polyester knitted mesh, polytetrafluoethylene (PTFE), expanded polytetrafluoethylene, polystyrene, nylon, polyethylene terephthalate, polyimide, polyethylene naphthalate, and polycarbonate. Examples of biopolymers include, without limitation, cellulose, collagen of human and/or animal origin.

Examples of resorbable materials include, without limitation, cellulose, polyglycolic acid, poly-γ-glutamic acid, polylactic acid, polyglactin 910, a polyhydroxylalkaoate derivative, a human amniotic membrane, a cow amniotic membrane, pig collagen, fibronectin, and dextran.

In some embodiments, the mesh may contain strands of nylon interwoven with strands of collagen. In other embodiments, the mesh may be a polypropylene/PTFE composite mesh, a polypropylene/cellulose mesh, a polyester/collagen mesh (e.g., PARIETEX™ composite (Sofradim, Trévoux, France)), polypropylene/SEPRAFILM™ mesh (e.g. SEPRAMESH™ (Genzyme, Cambridge, Mass.) and SEPRAMESH™ IP (Genzyme, Cambridge, Mass.)), a polypropylene/VICRYL™ mesh (e.g. VYPRO™ (Ethicon, Somerville, N.J.) and VYPRO™ II (Ethicon, Somerville, N.J.)), or a polypropylene/poliglecaprone mesh (e.g. ULTRAPRO™ (Ethicon, Somerville, N.J.)).

A pore size (porosity) of the mesh is the main determinant of tissue reaction toward the plate 100. The tissue reaction may involve inflammation, fibrosis, calcification, thrombosis and formation of granulomas. The extent of the reaction may be affected by the size of the plate, and/or when a mesh is present, the pore size of the mesh.

Pores of a mesh are preferably more than 75 µm in order to allow infiltration by macrophages, fibroblasts, blood vessels and collagen. Mesh substrates with larger pores (e.g. 0.5-5 mm, 1-4 mm, or 2-3 mm) allow increased soft tissue in-growth and are more flexible because of the avoidance of granuloma bridging, while a mesh with small pores develops stiff scar plates. Granulomas, which are masses of granulation tissue, normally form around individual mesh fibers as part of the foreign body reaction. Bridging describes the process whereby individual granulomas become confluent with each other and encapsulate the entire plate 100. This may lead to a stiff scar around plate 100 and a reduced flexibility and elasticity of the plate 100, which in turn may affect the vibration of the pancreas 104. In some embodiments, the pore size of the mesh substrate is 75 µm to 5 mm, 100 µm to 3 mm, 200 µm to 2 mm, 400 µm to 2 mm, 600 µm to 1.5 mm, 800 µm to 1 mm, or 1-5 mm, 2-4 mm.

The mesh may be modified in various ways to decrease the tissue reaction and increase biocompatibility. In one embodiment, the mesh may be coated with collagen, for example, to decrease visceral adhesion following implantation of the plate 100 (Collagen/Polypropylene composite mesh biocompatibility in abdominal wall reconstruction, Lukasiewicz A, Skopinska-Wisniewska J, Marszalek A, Molski S, Drewa T, Plast Reconstr Surg. 2013 May; 131 (5):731e-40e, incorporated herein by reference in its entirety). In another embodiment, the mesh may be coated with autologous platelets and blood plasma to increase the biocompatibility of the plate 100 (Coating with Autologous Plasma Improves Biocompatibility of Mesh Grafts In Vitro: Development Stage of a Surgical Innovation, Holger Gerullis, Evangelos Georgas, Christoph Eimer, Christian Arndt, Dimitri Barski, Bernhard Lammers, Bernd Klosterhalfen, Mihaly Borós, and Thomas Otto, BioMed Research International Volume 2013 (2013), Article ID 536814, 6 pages, incorporated by reference in its entirety). In still another embodiment, the mesh may be coated with cross-linked fish oil comprising cross-linked fatty acids and/or glycerides to provide anti-inflammatory, non-inflammatory, and anti-adhesion functionality, as disclosed in U.S. Pat. No. 8,574,627 B2, incorporated herein by reference in its entirety.

A weight of the mesh may range from 10-150 g/m$^2$, 30-120 g/m$^2$, 50-100 g/m$^2$, or 70-90 g/m$^2$. Heavier meshes have a higher tensile strength derived from a larger mass of material, which may activate a profound tissue reaction and dense scarring. When a less pronounced foreign body reaction and more elasticity of the mesh/plate 100 are desired, light-weight meshes of 10-50 g/m$^2$, 20-40 g/m$^2$ are preferred.

A mesh filament diameter may range from 0.05-0.30 mm, 0.08-0.2 mm, or 0.1-0.15 mm. A linear mass density of the mesh filament of the mesh may be in the range of 100-500 denier, 150-450 denier, or 200-400 denier.

The mesh may also cover at least a part of the surface of the motor, at least a part of the surface of the sensor, and/or at least a part of the surface of the internal unit to ensure these implanted elements are not rejected by the host. Alternatively, the surface of the implanted elements in contact with the tissue may be made of biocompatible metals, such as titanium and stainless steel, or covered in a silicone cover/sleeve.

The materials described herein may be relatively inert so they could remain in tissue without disturbing the physiology of the host (i.e., the subject). The implanted plate 100 (and/or other elements of the medical device) may elicit a foreign body reaction and may be subjected to an initial inflammatory phase where the host attempts to either eliminate or encapsulate the implanted plate. The inflammatory phase of healing lasts for about one week; the phase of fibrosis or collagen deposition begins and increases for a few weeks. Once encapsulation is complete, collagen deposition and degradation approach equilibrium and the scar matures within 30-60 days if the host is in good health and no outside forces influence the host-prosthesis interface.

Control of this inflammation and encapsulation may be achieved by altering the host-implant interface. It is hypothesized that when the outer surface is textured by a mechanical process to create a net-like textured surface, intertwining of the collagen and the interstices of the texture may occur thereby creating a mechanical bond between the tissue and the implant. Thus, an effective host-implant interface may be developed that may prevent unintended micromotion. That is, the texture on the implanted plate may promote adherence to the tissue and/or the pancreas 104 and may limit implant rotation within the host. A further advantage of a textured surface is that it may aid the host in isolating and destroying infection.

Figure 2A:
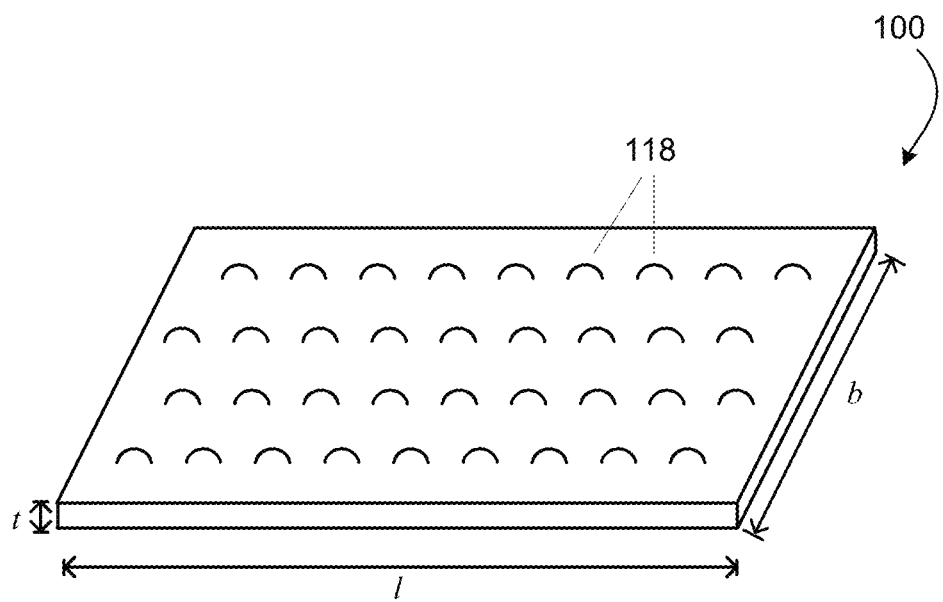
FIG. 2A shows an embodiment of a plate with a textured surface.
Figure 2B:
FIG. 2B shows a cross-sectional view of an embodiment of a plate with a tapered thickness.
Figure 2C:
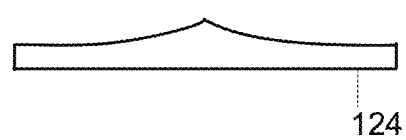
FIG. 2C shows a cross-sectional view of an embodiment of a plate with a tapered thickness.
Figure 2D:
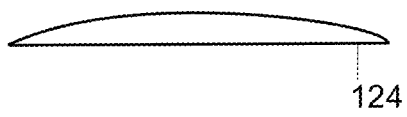
FIG. 2D shows a cross-sectional view of an embodiment of a plate with a tapered thickness.
Figure 4:
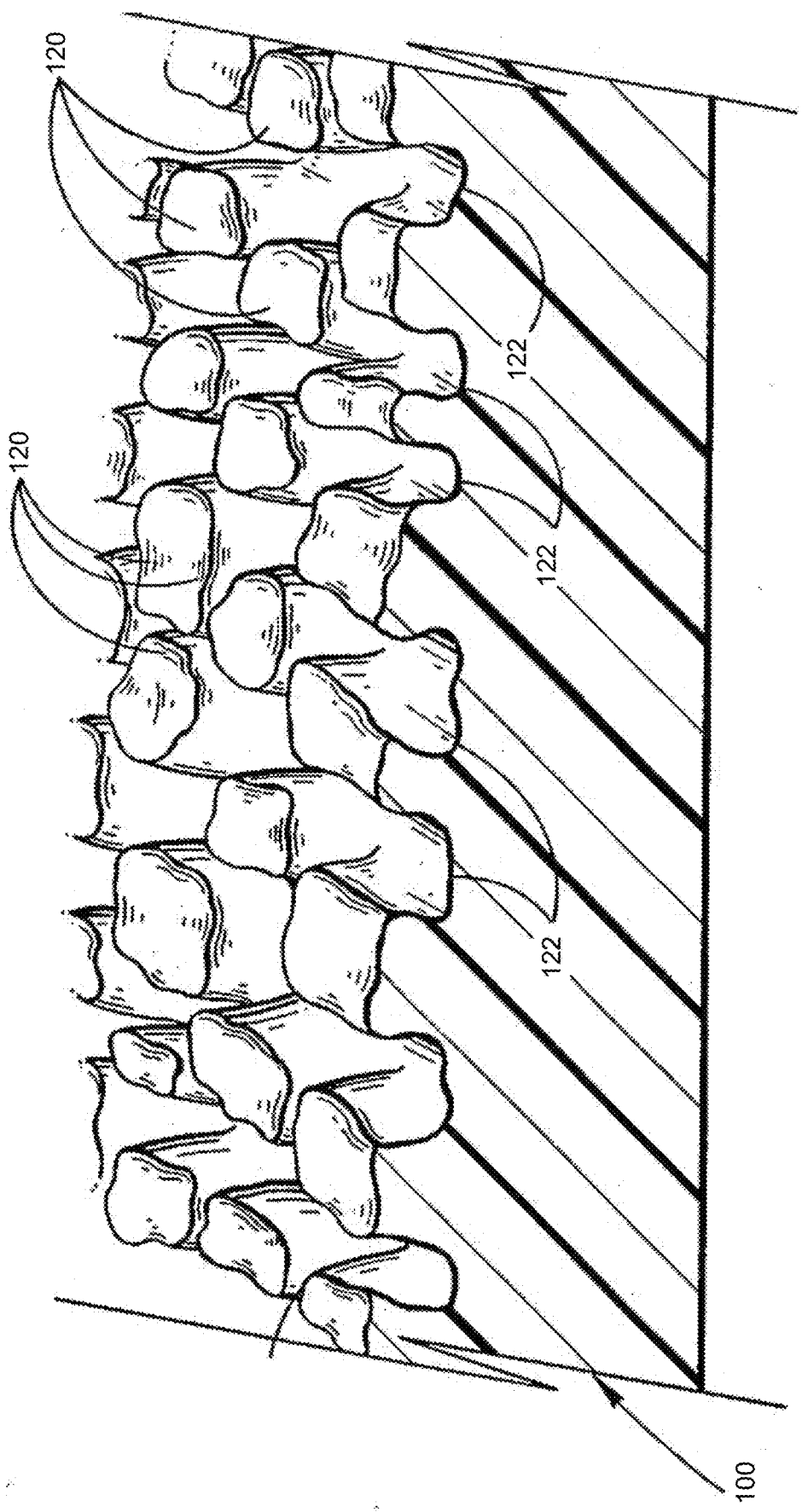
FIG. 4 shows another embodiment of a plate with a textured surface.
Figure 5:
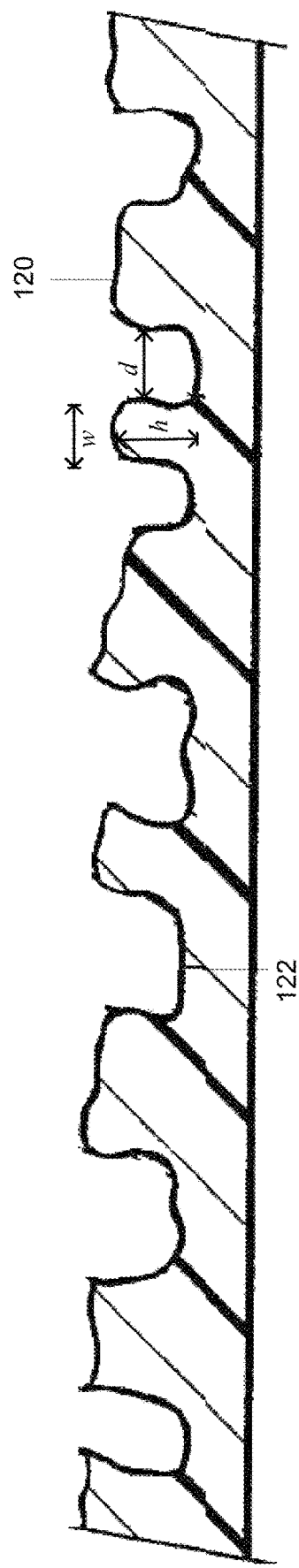
FIG. 5 shows a cross-sectional view of the plate shown in FIG. 4.

The surface of the plate 100 may have a plurality of concave, convex, ridge, pillar, or cylindrical microstructures. Such microstructures may help improve transmission of vibrational energy from the plate 100 to the pancreas 104. FIG. 2A shows a surface of the plate 100 containing convex microstructures (i.e., protrusions 118) in a shape of a hemisphere. In some embodiments, the convex microstructures may be in a shape of a triangle, rectangle, square, oval, pentagon, trapezium, or combinations thereof to effectively initiate the production of the insulin. FIG. 4 shows a surface of the plate 100 containing pillars 120 extending outwardly from a valley 122.

The human fibroblast is described as a pleomorphic cell of mesenchymal origin. This cell is approximately 20-100 µm in size. Therefore, in order to have any of the effects described herein (e.g., tissue ingrowth), the microstructures may be at least in the 20-100 µm range (e.g., the microstructures may have an average diameter, w, of 0.02-5 mm, 0.05-3 mm, 0.1-2 mm, or 0.5-1 mm). An average height, h, of the microstructures may be in a range of 0.02-2 mm, 0.05-1.5 mm, 0.1-1 mm, or 0.2-0.5 mm. Microstructures with an average height greater than 2 mm may alter the surface so drastically as to be seen or felt through the skin of a thin-skinned subject. An average distance, d, between each microstructure and an adjacent microstructure may be in a range of 5-100 µm, 10-80 µm, or 20-60 µm.

The microstructures may be formed with microthreads extending from the surface of the plate 100 at various lengths and having a diameter of 5-1,000 µm, 10-800 µm, 50-600 µm, 100-500 µm, 150-400 µm, or 200-300 µm. In some embodiments, the surface of the plate 100 may have a layer of fillers that protrude from the surface of the plate 100 at various heights to form a desired pattern of concave, convex, ridge, and/or cylindrical shaped topography to achieve the best possible form-fitting between the plate 100 and the implant site. In a preferred embodiment, the microthreads and the fillers are made of or coated with one or more biocompatible polymers such as alginate, hyaluronic acid, and collagen.

Figure 3:
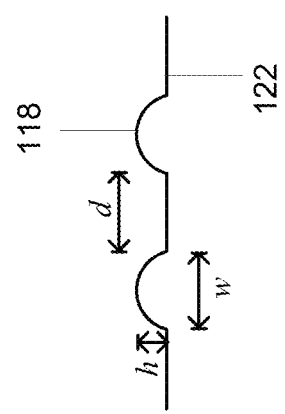
FIG. 3 shows a cross-sectional view of the plate shown in FIG. 2A.

The plate 100 containing microstructures may be made by using a mold having a surface arranged as the reverse image of the desired microstructures. Projections are present in the mold so as to create valleys 122 in the finished product, such as valleys 122 as illustrated in FIG. 3.

A plate 100 with a smooth surface may still function as intended. The average surface roughness ($R_a$) of the smooth plate 100 may be in a range of 0.01-5 µm, preferably 0.05-3 µm, more preferably 0.1-2 µm, and $R_z$ of the smooth plate 100 may be in a range of 0.05-5 µm, preferably 0.1-2 µm, more preferably 0.5-1 µm. As used herein, the term "$R_z$" refers to the average distance between the highest peak and the lowest valley in a sampling length according to American Society of Mechanical Engineers (ASME) Y14.36M-1996 Surface Texture Symbols (incorporated herein by reference in its entirety).

In some embodiments, the plate 100 comprises a reinforcing element in the plate so that the plate maintains its curve shape. The reinforcing element may increase the overall stiffness of the plate to an extent such that the reinforced plate resists deformation in response to the repeated vibrations. The reinforcing element may be made of a metal such as titanium, stainless steel, nickel, and copper. The reinforcing element may be in the form of a strip, a wire, or a mesh. When the reinforcing element is a strip or wire, it is oriented substantially parallel to the length of the plate. While the reinforcing element, when present, provides some degree of deformation resistance, it is desirable to maintain a low overall weight for the medical device. Therefore, the reinforcing element, when present, is preferably in the form of a small wire or a thin strip, and is preferably made of a light weight material such as titanium metal.

In some embodiments, the surface of the plate 100 in direct contact with the surface of the pancreas 104 is made of a soft material (e.g., silicone) which can protect the surface of the pancreas 104 when the pancreas is vibrating. In these embodiments, the silicone may be present as a layer of padding 102. The padding 102 may be smooth or have the plurality of microstructures on the surface in contact with the pancreas 104.

Glucose sensors may be used for determining the actual glucose level and providing feedback on the effects of the pancreatic treatment. Thus, for example, in a subject with weakened pancreatic response, the pancreas 104 may be stimulated to secrete more insulin when the glucose levels are too high (e.g., higher than 140 mg/dl, 160 mg/dl, or 190 mg/dl). Exemplary glucose sensors include, without limitation, an optical glucose sensor, a chemical glucose sensor, an ultrasonic glucose sensor, a heart rate glucose sensor, a biologic glucose sensor (e.g., encapsulated beta cells), and an electric glucose sensor (tracking beta cell and/or islet electrical behavior). The glucose sensor may be a blood glucose sensor.

Other types of sensors (e.g., a digestion sensor, a pancreatic activity sensor, an insulin sensor, a sensor for other pancreatic hormones) may be used in place of or with the glucose sensor.

Digestion sensors detect the ingestion (or intake) of meals and may prompt the production of insulin. Exemplary digestion sensors include, without limitation, impedance sensors that measure the stomach impedance, acceleration sensors that measure stomach or intestines movements, and electrical sensors that measure electrical activity. Digestion sensors may be problematic if they do not provide a measure of glucose actually ingested. In some embodiments, digestion sensors are used in combination with other sensors described herein.

Pancreatic activity sensors may be electrodes coupled to the entire pancreas 104, small parts of it, individual islet(s) or individual cell(s) in an islet. Such sensors are useful not only for providing feedback on the activity of the pancreas 104 and whether the applied vibration had a desired effect. Exemplary pancreatic activity sensors are described in the U.S. Patent Application Publication No. US 20070060812 A1, which is incorporated herein by reference.

Sensors for insulin and/or other pancreatic hormones (e.g., glucagon, pancreatic polypeptide, preproinsulin, proglucagon, somatostatin, vasoactive intestinal peptide, growth hormone releasing hormone, gastrin, and ghrelin), may also be used. Insulin sensors may be used to measure the response of a single islet, the pancreas 104 as a whole and/or to determine blood levels of insulin. The insulin sensor may be an electrochemical aptamer-based sensor. The aptamer may be the insulin-linked polymorphic region (ILPR) sequence, a G-rich sequence that presumably undergoes ligand-induced folding to form a G-quadruplex in presence of insulin.

The sensor 108 may monitor the level of the analyte (e.g. glucose, pancreatic hormones), food intake, and/or pancreatic activity automatically and/or throughout the day (e.g., every 1-60 minutes, 2-40 minutes, or 5-10 minutes). The sensor 108 may be powered by a battery (rechargeable or non-rechargeable) or external radio frequency sources (Young, D. J. et al., Lab Chip, 2015, 15, 4338-4347—incorporated herein by reference in its entirety).

The sensor 108 may be implanted (e.g., in the abdomen) or disposed external (e.g., worn on the wrist) to the subject. The sensor 108 may be wired to or in wireless communication with the control unit 112 or the internal unit 110. For example, a wireless sensor 108 may be used (Tee, C. et al., US Patent Application 20140350348A1; Poon, A. et al., WIPO Patent Application WO2014071079 A1—each incorporated herein by reference in its entirety). The wireless sensor 108 may comprise an antenna and/or a transceiver. The sensor 108 may be configured to receive wireless power, communicate the detected level of analyte, food intake, and/or pancreatic activity to the control unit 112 or the internal unit 110, and receive instructions in varying the monitoring frequency.

A length of the motor 106 may be 3-20 mm, 6-15 mm, or 11-12 mm. A width of the motor 106 may be 0.5-15 mm, 6-12 mm, or 10-11 mm. A height of the motor 106 may be 0.5-15 mm, 5-12 mm, or 8-11 mm. The motor 106 may be in direct contact with at least one plate 100. The motor 106 may have at least one eye bolt or a screw eye which is integral to the motor 106. The motor 106 may be attached to the at least one plate 100 by stitching, staples, tacks, and/or hooks via the eye bolt or the screw eye. In some embodiments, the motor 106 may be covered in a silicone cover/sleeve which is integral with the plate 100. In some embodiments, there may be one motor 106 per plate 100 and may be disposed on the center of the at least one plate 100. The motor 106 may be disposed 0.5-8 mm, 1-6 mm, or 2-3 mm from a length of the plate 100 and/or 1-20 mm, 2-15 mm, or 5-10 mm from a breadth of the plate 100 and the device may still function as intended. In some embodiments, there may be 2-5, or 3-4 motors per plate and the motors may be evenly distributed over the length of the plate 100 to ensure uniform vibration throughout the plate 100. In these embodiments, the motor 106 may have an antenna so that the motor 106 may be actuated and deactuated remotely. The motor 106 may be battery-operated. The battery may be a non-rechargeable battery and the battery life may be up to 10 years, for example 1-5 years, or 2-4 years. When the battery life is low, the motor 106 may need to be replaced. In some embodiments, the battery may be a rechargeable battery which may be recharged by radio frequency. In these embodiments, the antenna receives the radio frequency signal and feeds it to a rectifying circuit, which turns the signal into direct current to charge the battery.

In some embodiments, there is a vibration transfer medium between the motor 106 and the at least one plate 100. The vibration transfer medium transfers the vibrations from the motor 106 to the plate 100 and may be in a form of a rod (111) or a block. When the vibration transfer medium is a rod, a first circular face of the rod (111) is in direct contact with the motor 106 and the second circular face is in direct contact of the plate 100. The vibration transfer medium may contain at least one eye bolt or a screw eye which is integral to the vibration transfer medium. The vibration transfer medium may be attached to the at least one plate 100 and the motor 106 by stitching, staples, tacks, and/or hooks via the eye bolt or the screw eye. There may be 1 vibration transfer medium per motor. In some embodiments, there are 2-5, or 3-4 vibration transfer mediums per motor.

The motor 106 may be commercially available and known to those skilled in the art. For example, the motor 106 may be a micro vibration motor or an ultrasound transducer. When the micro vibration motor is actuating, the speed may be 0.1-10 mm/s, 0.5-5 mm/s or 1-3 mm/s. The pancreas 104 may be vibrating at a frequency of 50-100 Hz, 60-90 Hz, or 78-80 Hz. The ultrasound transducer may operate at a low frequency, such as 20-100 kHz, 30-70 kHz, or 40-60 kHz, and the pancreas 104 may be vibrating at the same frequency. A waveform of the ultrasonic wave may be a sawtooth wave, a square wave, or combinations thereof.

The control unit 112 may contain a display 114 (e.g., a LED or LCD display), at least one battery 116 (rechargeable or non-rechargeable), a transceiver, and an electronic board that includes a central processing unit (CPU) 600, and a memory chip. The control unit 112 provides the user interface of the medical device. For example, the subject may enter the monitoring frequency of the sensor 108 using the control unit 112. The CPU 600 may be electrically connected to the motor and the glucose sensor. Thus, the CPU 600 may be responsible for carrying out the instructions needed to run the motor 106 intermittently and as needed to keep blood glucose within the acceptable range. For example, the CPU 600 sends the signal to actuate and deactuate the motor depending on the blood glucose level. The control unit 112 may be configured to provide wireless power to the antenna of the wireless sensor 108 and/or the motor 106.

Suitably, the control unit 112 produces an indication, such as a sound signal and/or displayed information and/or a vibration, in situations where: (1) the batteries in the motor 106/sensor 108/control unit 112 are low in power, (2) the level of analyte exceeds the predetermined threshold, and/or (3) the motor 106 is about to be actuated. The control unit 112 may be attached to the subject's clothes, preferably near the inguinal region, by clips to facilitate removal of the control unit 112 when necessary. In some embodiments, the medical device may contain an implantable and programmable internal unit 110, such as a microprocessor, which may be in communication with the sensor 108, the motor 106, and the control unit 112. The internal unit 110 may be configured to receive wireless power and/or data (e.g., detected level of analyte, food intake, and/or pancreatic activity) from the sensor 108; and communicate the data to the control unit 112. The internal unit 110 may control the actuation and deactuation of the motor 106 in response to the signals from the sensor 108. For example, when the blood glucose level is higher than 140 mg/dl, the control unit 112 sends a signal to the internal unit 110 to actuate the motor 106. Subsequently, the motor 106 is actuated thereby vibrating the at least one plate 100, which in turn vibrates the pancreas 104. The pancreas 104 may be vibrated for an effective duration until the blood glucose level is within 70-140 mg/dl. The effective duration may be in a range of 1 second to 30 minutes, 10 seconds to 20 minutes, or 1-10 minutes. The internal unit 110 also works as an energy receiver, i.e., for transforming wireless energy into electric energy which is used to charge the rechargeable battery. The internal unit 110 may be implanted subcutaneously or in the abdomen. In one embodiment, the internal unit 110 comprises at least one transceiver to transmit and receive wireless energy from the control unit 112 and/or the sensor 108. For example, the transceiver in the internal unit 110 may send a signal to the control unit 112 in response to signals from the sensor 108. The transceiver in the internal unit 110 may receive monitoring frequency instructions from the control unit 112 and relay such instructions to the sensor 108.

In one embodiment, the control unit 112 is in the form of a hand-held control unit 112 or an application in electronic devices such as a phone, a tablet and/or a watch. The control unit 112 may comprise at least one external signal transmitter or transceiver and at least one internal signal receiver or transceiver implantable in the subject. The control unit 112 preferably transmits at least one wireless control signal for controlling the internal unit 110. The wireless control signal may comprise a frequency, amplitude, phase modulated signal, or combination thereof. Alternatively, the control unit 112 transmits an electromagnetic carrier wave signal for carrying the control signal. The control signal comprises an analogue signal, a digital signal, or a combination of an analogue and digital signal. The control unit 112 may be adapted to set the control parameters of the medical device from outside the subject without mechanically penetrating the subject. At least one of the control parameters, which may be set by the control unit 112, is the predetermined threshold value of the analyte/pancreatic activity/food intake, and the monitoring frequency for the sensor 108. Alternatively, the control unit 112 may be replaced by a subcutaneously implanted push button that is manually switched by the subject between "on" and "off". Such a manually operated push button may also be provided in combination with the control unit 112 as an emergency button to allow the patient to stop the operation of the medical device in case of emergency or malfunction. To avoid accidental/premature switch-off, the medical device may be equipped with a push button safety mechanism that involves a particular push button combination or sequence for effecting device shut-off, for example, pushing the push button 4 times or pressing the push button continuously for 5 seconds.

Figure 6:
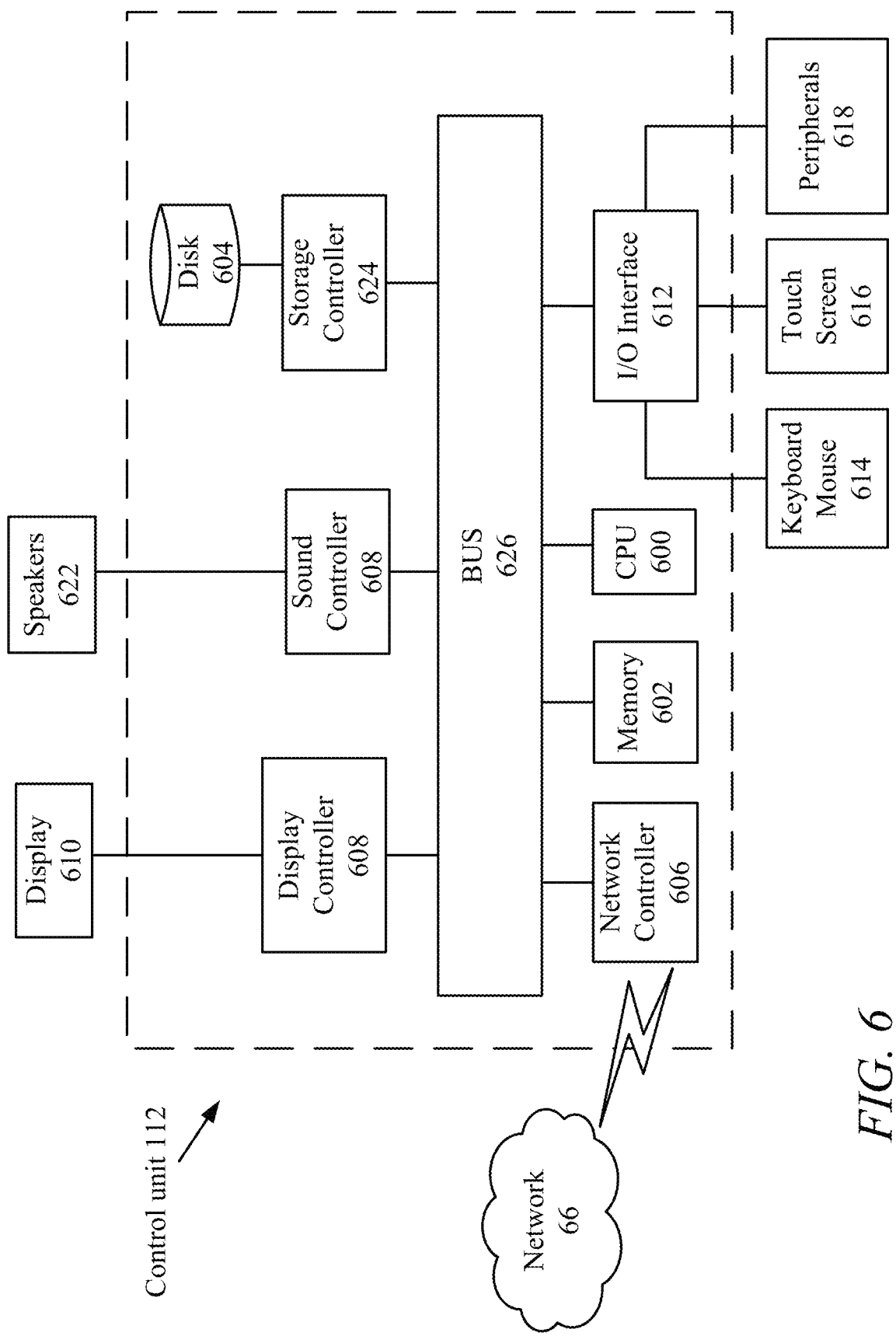
FIG. 6 shows the elements present in an embodiment of the control unit.

Next, a hardware description of the control unit 112 according to exemplary embodiments is described with reference to FIG. 6. In FIG. 6, the control unit 112 includes a CPU 600 which performs the processes described above/below. The process data and instructions may be stored in memory 602. These processes and instructions may also be stored on a storage medium disk 604 such as a hard drive (HDD) or portable storage medium or may be stored remotely. Further, the claimed advancements are not limited by the form of the control unit 112—readable media on which the instructions of the inventive process are stored.

For example, the instructions may be stored on CDs, DVDs, in FLASH memory, RAM, ROM, PROM, EPROM, EEPROM, hard disk or any other information processing device with which the control unit 112 communicates, such as a server or control unit 112.

Further, the claimed advancements may be provided as a utility application, background daemon, or component of an operating system, or combination thereof, executing in conjunction with CPU 600 and an operating system such as Microsoft Windows 7, UNI6, Solaris, LINU6, Apple MAC-OS and other systems known to those skilled in the art.

The hardware elements in order to achieve the control unit 112 may be realized by various circuitry elements, known to those skilled in the art. For example, CPU 600 may be a 6enon or Core processor from Intel of America or an Opteron processor from AMD of America, or may be other processor types that would be recognized by one of ordinary skill in the art. Alternatively, the CPU 600 may be implemented on an FPGA, ASIC, PLD or using discrete logic circuits, as one of ordinary skill in the art would recognize. Further, CPU 600 may be implemented as multiple processors cooperatively working in parallel to perform the instructions of the inventive processes described above.

The control unit 112 in FIG. 6 also includes a network controller 606, such as an Intel Ethernet PRO network interface card from Intel Corporation of America, for interfacing with network 66. As can be appreciated, the network 66 can be a public network, such as the Internet, or a private network such as an LAN or WAN network, or any combination thereof and can also include PSTN or ISDN sub-networks. The network 66 can also be wired, such as an Ethernet network, or can be wireless such as a cellular network including EDGE, 3G and 4G wireless cellular systems. The wireless network can also be WiFi, Bluetooth, or any other wireless form of communication that is known.

The control unit 112 further includes a display controller 608, such as a NVIDIA GeForce GT6 or Quadro graphics adaptor from NVIDIA Corporation of America for interfacing with display 114/610. A general purpose I/O interface 612 interfaces with a keyboard and/or mouse 614 as well as a touch screen panel 616 on or separate from display 114/610. General purpose I/O interface also connects to a variety of peripherals 618 including printers and scanners, such as an OfficeJet or DeskJet from Hewlett Packard.

A sound controller 620 is also provided in the control unit 112, such as Sound Blaster 6-Fi Titanium from Creative, to interface with speakers/microphone 622 thereby providing sounds and/or music.

The general purpose storage controller 624 connects the storage medium disk 604 with communication bus 626, which may be an ISA, EISA, VESA, PCI, or similar, for interconnecting all of the components of the control unit 112. A description of the general features and functionality of the display 114/610, keyboard and/or mouse 614, as well as the display controller 608, storage controller 624, network controller 606, sound controller 620, and general purpose I/O interface 612 is omitted herein for brevity as these features are known.

The medical device may be useful for inducing the release of antibodies, endorphins, or enzymes from other organs (e.g., stomach, liver, large intestine), tissue, and/or the skeletal structure, to fight other ailments or diseases. The medical device may be useful for enhancing the function of other internal body organs and glands. For example, the medical device may be useful for improving bowel movement and relief constipation when the at least one plate 100 is in direct contact with a surface of the large intestine.

The invention claimed is:

1. A medical device, comprising:
a glucose sensor;
a single vibration motor, wherein the vibration motor is an ultrasonic transducer configured to vibrate at 40-60 kHz, wherein the plate has a single inner surface and a single outer surface;
a single plate, wherein the plate is connected to the motor through a rod having first and second circular faces, wherein the first circular face of the rod is in direct contact with the vibration motor and the second circular face is in direct contact with the plate, and the plate and motor are implantable in a patient;
a control unit in communication with the motor and the glucose sensor,
wherein the plate is configured to conform to a surface of a pancreas of the patient and the entire inner surface of the plate has a microstructured surface that is configured to be in continuous contact with the surface of the pancreas of the patient, wherein the plate has a continuous curve structure configured to conform with a shape of the pancreas so that an apex of the curve structure is configured to cover a head portion of the pancreas and a chord of the curve corresponds with a tail portion of the pancreas, wherein the vibration motor is connected to the plate at the apex of the curve structure and the plate has a longitudinal axis configured to be parallel to a longitudinal axis of the pancreas;
wherein the plate is configured to be between the vibration motor and the surface of the pancreas and the entire inner surface of the plate is configured to be in contact with the surface of the pancreas,
wherein the microstructured surface has a pattern of repeating microstructure protrusions having an average height of 0.02-2 mm and an average distance between each microstructure protrusion and an adjacent microstructure protrusion is in a range of 5-100 μm, and
wherein the plate has a length in a range of 15-50 mm, a width in a range of 1-25 mm and a thickness in a range of 0.1-2 mm.

2. The medical device of claim 1, wherein the plate is flexible.

3. The medical device of claim 1, wherein the plate comprises silicone.

4. The medical device of claim 1, wherein the control unit comprises:
a display;
at least one battery; and
a central processing unit electrically connected to the vibration motor and the glucose sensor.

5. The medical device of claim 1, wherein the control unit is configured to actuate and deactuate the vibration motor based on a blood glucose level feedback from the glucose sensor, thereby keeping a blood glucose level within a range of 70-140 mg/dl.

6. The medical device of claim 1, wherein the microstructure protrusions are made of or coated with one or more selected from the group consisting of alginate, hyaluronic acid and collagen.

7. The medical device of claim 1, wherein the chord of the curve is in a range of from 0.2-3 mm.

* * * * *